United States Patent [19]

Luther et al.

[11] Patent Number: 5,273,540
[45] Date of Patent: Dec. 28, 1993

[54] NONREUSABLE NEEDLE AND CATHETER ASSEMBLY

[75] Inventors: Ronald B. Luther, Newport Beach, Calif.; Cynde L. Luther, Broomfield, Colo.

[73] Assignee: Luther Medical Products, Tustin, Calif.

[21] Appl. No.: 692,243

[22] Filed: Apr. 26, 1991

[51] Int. Cl.$^5$ .............................................. A61M 5/00
[52] U.S. Cl. .................................. 604/110; 604/192; 604/198
[58] Field of Search ............... 604/110, 162, 167, 171, 604/192, 197, 198, 263

[56] References Cited

U.S. PATENT DOCUMENTS

| | | | |
|---|---|---|---|
| 561,059 | 5/1896 | Mitchell | 604/162 |
| 4,525,157 | 6/1985 | Vaillancourt | 604/171 |
| 4,664,654 | 5/1987 | Strauss | 604/198 |
| 4,770,655 | 9/1988 | Haber et al. | 604/110 |
| 4,887,998 | 12/1989 | Martin et al. | 604/110 |
| 4,927,415 | 5/1990 | Brodsky | 604/171 |
| 4,944,728 | 7/1990 | Carrell | 604/110 |
| 4,966,592 | 10/1990 | Burns et al. | 604/263 |
| 4,994,041 | 2/1991 | Dombrowski | 604/198 |
| 4,994,046 | 2/1991 | Wesson et al. | 604/263 |
| 5,002,533 | 3/1991 | Jullien | 604/110 |
| 5,026,353 | 6/1991 | Bartman | 604/263 |
| 5,037,402 | 8/1991 | Bartman | 604/198 |

FOREIGN PATENT DOCUMENTS 9007349 7/1990 World Int. Prop. O. .......... 604/197

Primary Examiner—C. Fred Rosenbaum
Assistant Examiner—Ronald Stright, Jr.
Attorney, Agent, or Firm—Stetina and Brunda

[57] ABSTRACT

A needle-safe flashback chamber for vascular/venous access devices wherein the needle cannula is automatically captured within a protective sheath upon being withdrawn from the patient to prevent accidental exposure of administering personnel to substantial health risk, such as that associated with the AIDS virus, hepatitis, and other infectious diseases is comprised of a needle cannula; a substantially transparent reservoir in fluid communication with the needle cannula; a vent formed in the cavity; and a substantially transparent sheath, sized and configured to slidably receive the needle cannula and cavity. The transparent reservoir can be partially withdrawn from the sheath, simultaneously withdrawing the needle cannula into the sheath. The needle cannula is attached to the cavity at an angled offset from the longitudinal axis of the cavity such that when the reservoir is withdrawn a sufficient distance from the sheath, the tip of the needle cannula will become axially misaligned with the needle cannula aperture formed therein, thereby preventing reextension of the needle cannula.

22 Claims, 1 Drawing Sheet

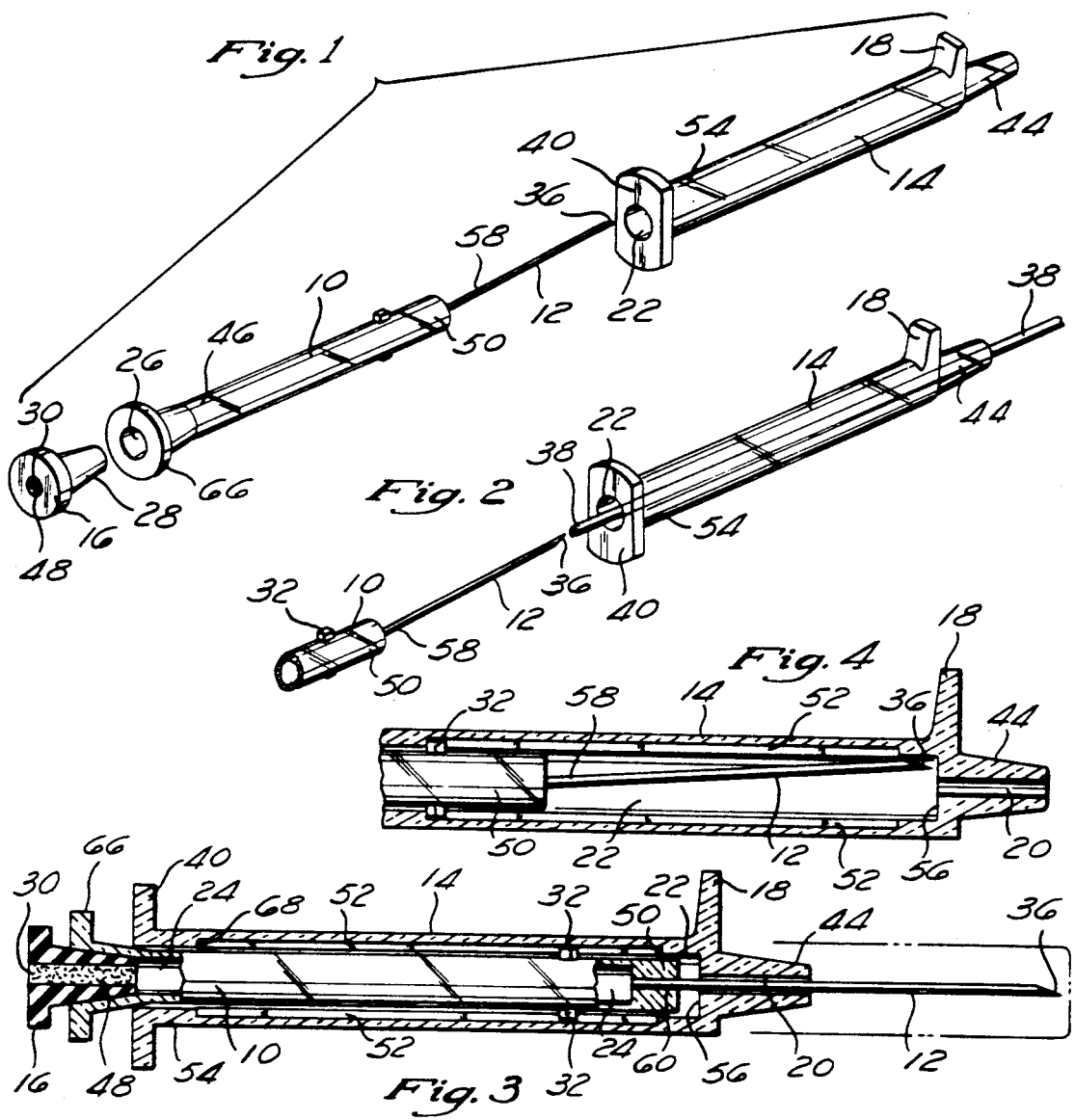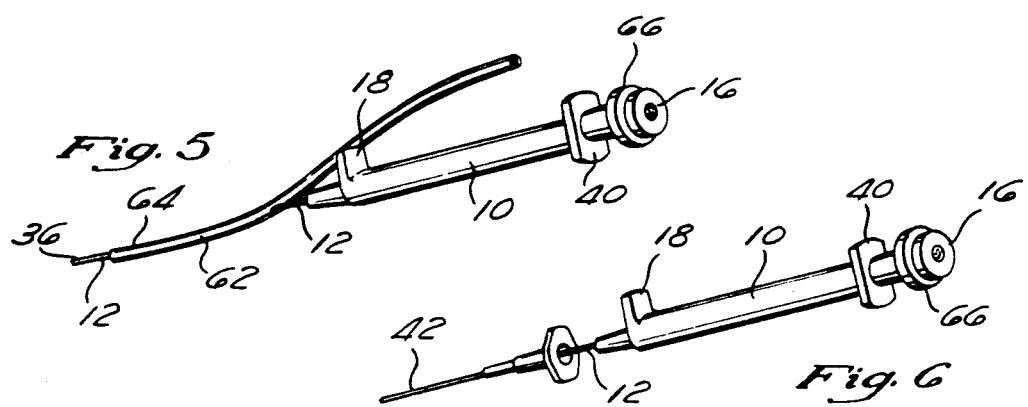

NONREUSABLE NEEDLE AND CATHETER ASSEMBLY

FIELD OF THE INVENTION

The present invention relates generally to medical insertion devices and more particularly to a needle-safe flashback chamber for a venous or vascular access device wherein the needle cannula is automatically captured within a protective sheath upon being withdrawn from the patient to prevent accidental exposure of administering personnel to substantial health risks, such as those associated with the AIDS virus, hepatitis, and other infectious diseases.

BACKGROUND OF THE INVENTION

Vascular/venous access devices for introducing catheters into a patient's vascular system are well known. The simplest of such devices comprises a through-the-needle catheter having a cannula which generally comprises a metal needle inserted into the patient's vein and through which a catheter may subsequently be introduced. A common problem associated with the use of such prior art through-the-needle catheter systems arises in removing the cannula after the catheter has been introduced into the vein. Since the cannula is typically comprised of a rigid metal needle, it is desirable to remove the cannula from the patient's vein after insertion of the catheter to prevent trauma to the vein caused by the cannula's rigid structure and/or sharp tip. However, once the catheter has been inserted into the vein, the cannula can typically only be removed by retracting the same upwardly along the catheter, thereby exposing the patient as well as administering personnel to accidental contact with the cannula.

In recognizing the discomfort and extraction problems of the cannula associated with through the needle catheter systems, over-the-needle catheter systems have been widely utilized for venous access applications. In such over-the-needle catheter systems, a thin catheter having a hub at its proximal end is placed over a rigid cannula, such as a needle, whereby the cannula as well as the catheter may be simultaneously inserted into the vein of a patient. Once the cannula and catheter and have been introduced into the vein, the cannula may be withdrawn from the interior of the catheter leaving the catheter disposed within the patient's vein. Subsequently, required administration line communication can be effectuated with the catheter by interconnection with its hub mounted to the proximal end of the catheter. However, due to such over-the-needle catheters being inserted into the vein of the patient concurrently with the rigid cannula, such over-the-needle catheters must possess sufficient rigidity to prevent the same from traveling axially upward relative the cannula during the insertion process. As such, such over-the-needle catheters are limited in their axial length and are incapable of being inserted upwardly through the length of the vein or artery without causing trauma and/or puncture to the vein.

In recent years, the desirability of utilizing a peripherally inserted central catheter (PICC) line into a patient for medical applications has become widespread. In such PICC line applications, a flexible catheter must be introduced into the vascular system of a patient and subsequently be manipulated to allow the catheter to wind its way upwardly through the vascular system to a desired location. Due to the requirement of advancing the catheter upwardly the vascular system, the catheter must be formed from a soft, biocompatible, pliable, and flexible material which is capable of winding through and extending through substantial axial lengths of the vascular system, i.e. from two to thirty inches or more, without causing trauma to the vascular system or puncturing therethrough. In view of such requirements, heretofore, through-the-needle catheter systems have been typically utilized wherein after venous insertion, the cannula is retained within the patient and the desired length of catheter is inserted through the cannula and into the vein of the patient. In such applications, blood leakage is commonplace which exposes administering personnel to substantial health risks, such as that associated with the AIDS virus, hepatitis, and other infectious diseases.

In view of these concerns, recently an over-the-needle catheter system has been introduced specifically adapted for PICC line applications which attempts to minimize accidental exposure of medical personnel to patient's blood. This particular venous access device is manufactured by Menlo Care, Inc. of Palo Alto, California and is marketed under the trademark LANDMARK venous access device.

Additionally, in recognizing the desirability of providing an improved vascular/venous access device which would permit the introduction of an unlimited length of catheter into a patient's vascular system and which facilitates removal of the needle to prevent accidental punctures and/or exposure; which is simple and inexpensive to fabricate; and which requires a minimum of training and manipulative skill to practice, Applicant previously invented an improved vascular/venous access device. The improved vascular/venous access device allows insertion of a flexible over-the-needle catheter of unlimited axial length utilizing a relatively short cannula and facilitates removal of the cannula from the catheter. The improved vascular/venous access device is described in Applicant's U.S. patent application Ser. No. 07/669,679, filed Mar. 4, 1991, now U.S. Pat. No. 5,112,312 entitled VASCULAR/VENOUS ACCESS DEVICE AND METHOD OF UTILIZING AND FORMING THE SAME, the entire disclosure of which is expressly incorporated herein by reference. In this vascular/venous access device the distal or sharp end of a needle cannula extends outwardly from the distal end of the catheter and the proximal end of the needle cannula exits the central bore of the catheter through a hole or slit formed in the side wall a short distance from the distal end of the catheter. A gripping device selectively locks the needle cannula in place within the bore of the catheter and provides a means for gripping the venous access device during insertion of the needle cannula and catheter into a patient's vein, artery, or the like.

The needle cannula provides a rigid and sharp implement for effecting entry into the patient's vascular system. After the needle cannula and catheter have entered the vascular system, the needle cannula is withdrawn from the catheter and the gripping device may be removed or alternatively used as a catheter guide or tape site. The desired length of the catheter may then be manually advanced into the vascular system to a desired position.

The catheter is preferably formed having a generally rigid tip portion disposed along a substantial length of the needle cannula with the remaining length of the catheter being formed having a soft flexible configuration. The rigid portion prevents buckling and/or axial compression of the catheter during the insertion process and subsequently softens upon contact with blood and/or liquids introduced via administration through the catheter or from the thermal gradient caused from patient residence such that a soft flexible tip is then provided for manipulation of the catheter within the vascular system.

The catheter is preferably formed by a sequential mandrel dip process. More particularly, the rigid tip portion may be formed by dipping a mandrel into a solubilized softenable material and allowing the softenable material to dry on the mandrel. The softenable material is preferably hydrated from the mandrel and the desired length for the distal tip portion is cut off. This distal portion is then applied to and dried on a secondary dipping mandrel and a length of flexible catheter is inserted over the mandrel such that the catheter abuts the softenable distal portion. The softenable portion and the portion of flexible catheter are then dipped into a liquid polymer such that the two portions are solvent welded together and an outer layer of polymer is deposited thereover. Thus a contiguous assembly is formed by bonding the softenable material to the distal end of the flexible catheter. The assembly is then allowed to dry and the dipped softenable tip portion is trimmed to exhibit a profile that facilitates insertion into a patient. The mandrel is subsequently removed from the assembly of the catheter and the softenable portion such that a continuous lumen is formed within both portions. A needle cannula is then inserted through the wall of the catheter and extended axially through the length of the catheter such that its sharp tip extends outwardly beyond the softenable end of the catheter.

A flashback chamber is commonly used with vascular/venous access devices, such as that of Applicant's above-described prior invention, to provide an indication that the tip of the needle cannula has entered a vein. Entry of the tip of the needle cannula into a vein is indicated by flashing or blood entering the flashback chamber. The flashback chamber contains the blood, thus reducing health risks and preventing spillage. The flash chamber is attached to and in fluid communication with the needle cannula and may be formed as an integral part thereof.

In the vascular/venous access device of pending U.S. patent application Ser. No. 07/669,679, the needle cannula may be exposed after it is withdrawn from the catheter, thus presenting a possible health risk to administering personnel. In contemporary over-the-needle insertion devices the needle is similarly exposed after being withdrawn for disposal.

In view of the shortcomings of the prior art, it is desirable to provide a needle-safe flashback chamber for use with vascular/venous access devices wherein the needle cannula is automatically captured within a protective sheath upon being withdrawn from the patient to prevent accidental exposure of administering personnel to substantial health risks, such as that associated with the AIDS virus, hepatitis, and other infectious diseases.

SUMMARY OF THE INVENTION

The present invention specifically addresses and alleviates the above-mentioned deficiencies associated in the prior art. More particularly, the present invention comprises a needle-safe flashback chamber for vascular/venous access devices wherein the needle cannula is automatically captured within a protective sheath upon being withdrawn from the patient to prevent accidental exposure of administering personnel to substantial health risks, such as those associated with the AIDS virus, hepatitis, and other infectious diseases. The needle-safe flashback chamber of the present invention is comprised of a needle cannula; a substantially transparent reservoir in fluid communication with the needle cannula; a vent formed in the reservoir; and a substantially transparent sheath, sized and configured to slidably receive the needle cannula and reservoir. The transparent reservoir can be partially withdrawn from the sheath, simultaneously drawing the needle cannula into the sheath. The needle cannula is attached to the reservoir at an angle offset from the longitudinal axis of the reservoir such that when the reservoir is withdrawn a sufficient distance from the sheath, the tip of the needle cannula will become axially misaligned with a needle aperture formed therein, thereby preventing re-extension of the needle cannula through the needle aperture. These, as well as other advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is an exploded perspective view of the needle-safe flashback chamber for vascular/venous access devices according to the present invention;

FIG. 2 is the needle-safe flashback chamber of FIG. 1 showing the insertion of an assembly tube into the sheath to facilitate insertion of the needle cannula therein during the assembly process;

FIG. 3 is a cross-sectional side view of the needle-safe flashback chamber of FIG. 1 showing the sheath disposed in its non-protecting position as when the flashback chamber is ready for use;

FIG. 4 is a cross-sectional side view of the forward portion of the needle-safe flashback chamber of FIG. 1 showing the sheath disposed in its protecting position as after the device has been used;

FIG. 5 is a perspective view of the needle-safe flashback chamber of the present invention being used in accordance with Applicant's invention of VASCULAR/VENOUS ACCESS DEVICE; and FIG. 6 is a perspective view of the needle-safe flashback chamber of the present invention being used with a contemporary over-the-needle venous access device.

DETAILED DESCRIPTION OF THE PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The needle-safe flashback chamber of the present invention is illustrated in FIGS. 1-6 which depict a presently preferred embodiment of the invention. Referring now to FIG. 1, the needle-safe flashback chamber is generally comprised of an elongate, substantially transparent reservoir 10, a needle cannula 12 in fluid communication with the reservoir 10 and attached thereto, and a sheath 14 into which the reservoir 10 is slidably disposable. The sheath 14 has a non-protecting position (as shown in FIG. 3) relative to the needle cannula 12 in which the needle cannula 12 extends from the sheath 14 such that the flash chamber is configured for use. The sheath 14 also has a protecting position (as shown in FIG. 4) relative to the needle cannula 12 in which the needle cannula 12 is captured within the sheath 14 such that administering personnel are protected from accidental puncture or other exposure to the needle cannula 12.

The needle cannula 12 is attached to the reservoir 10 at an angle offset from the longitudinal axis of the reservoir 10 such that disposing the sheath 14 in the protecting position causes the needle cannula 12 to exit the needle aperture 20 formed at the distal end 44 of the sheath 14 and move to a position such that an attempt to dispose the sheath 14 in the non-protecting position results in misalignment of the needle cannula 12 and the needle aperture 20 to lock the sheath 14 in the protecting position. This will be discussed in further detail infra.

A plug 28, preferably generally conical in shape, engages an aperture, preferably a Luer lock 26, formed at the proximal end 46 of the reservoir 10. The conical plug 28 comprises a vent 30 containing a filter 48 (best shown in FIG. 3). The filter 48 preferably comprises a porous or fibrous hydrophobic material which readily permits the flow of air therethrough while inhibiting the flow of blood. Those skilled in the art will recognize that various filter materials are suitable. A flange 16 formed upon the plug 28 provides a convenient finger hold for removing the plug 28 from the conical aperture or Luer lock 26.

A forward finger stop 18 extends from the distal end 44 of the sheath 14 and provides a convenient means for manually urging the needle cannula 12 into a patient's vein. Typically, the tip of the user's index finger will abut the forward finger stop 18 to apply forward pressure to the device during insertion. The cap 16 of the reservoir 10 may abut the palm of the user's hand to prevent the reservoir 10 from being inadvertently withdrawn from the sheath 14 during insertion. Rear finger stop 40 extends from the proximal end 54 of the sheath 14 and provides a convenient hold for extracting the needle cannula 12 from the patient's vein.

Referring now to FIG. 2, assembly of the needle cannula 12 and reservoir 10 into the sheath 14 is illustrated. A tube 38 is installed temporarily through the needle bore 20 (best shown in FIG. 4) and reservoir bore 22 of the sheath 14 to serve as a tool to guide the angle offset needle cannula 12 through the needle bore 20 during assembly. This is necessary because the angle offset of the needle cannula 12 relative to the longitudinal axis of the elongate reservoir 10 would otherwise cause the needle cannula 12 to be misaligned with the needle bore 20. Such misalignment, identical to that encountered after the sheath is moved to the protecting position after use, is illustrated in FIG. 4. Thus, the tube 38 receives the needle cannula 12 and then the reservoir 10 and needle cannula 12 are manipulated into the reservoir bore 22. The needle cannula 12 is urged forward such that it extends through the needle bore 20 and the tube 38 is then removed.

During assembly the detents 32 may be forced into the bore 22 of the reservoir 14 wherein they will engage the channels 52 (best shown in FIGS. 3 and 4) thereof. This is possible because both the reservoir 10 and the sheath 14 are preferably comprised of a moderately pliable plastic material, such as polyethylene. The forward edges of the detents 32 may be beveled to facilitate insertion into the bore 22.

Referring now to FIG. 3, the assembled needle-safe flashback chamber of the present invention is shown in cross-section. The needle cannula 12 extends through the needle bore 20 of the sheath 14 and the substantially transparent reservoir 10 is disposed within the reservoir bore 22 of the sheath 14. Reservoir detents 32 are formed upon the reservoir 10 near its distal end 50 where they contact and frictionally engage channels 52 formed in the reservoir bore 22 of the sheath 14. The channels 52 extend a substantial portion of the length of the reservoir bore 22 of the sheath 14. Engagement of the reservoir detents 32 with the channels 52 prevents rotation of the reservoir 10 relative to the sheath 14. Rotation of the reservoir 10 relative to the sheath 14 is prevented because of the desirability of maintaining a given orientation of the tip 36 as the needle cannula 12 is being inserted into a patient's vein. As those skilled in the art are aware, it is generally desirable to maintain the open face of the needle cannula 12 upward, away from the skin, during insertion.

Thus, the reservoir detents 32 cooperate with the channel 52 to define a guiding means which prevents the reservoir 10 from being rotated relative to the sheath 14 and also prevents the reservoir 10 from being fully withdrawn from the sheath 14 to expose the needle cannula 12. Those skilled in the art will recognize that various channel and/or detent means are suitable for preventing rotation of the reservoir 10 and/or for locking the reservoir 10 within the sheath 14.

Referring now to FIG. 4, withdrawal of the reservoir 10 from the sheath 14 results in misalignment of the tip 36 of the needle cannula 12 with the needle bore 20 such that the needle cannula 12 cannot be reinserted into the needle bore 20 by merely urging the reservoir 10 into the sheath 14. This locks the sheath 14 into its protecting position. It eliminates the substantial health risks associated with the AIDS virus, hepatitis, and other infectious diseases since the potentially contaminated needle cannula 12 cannot contact administering personnel once the sheath is disposed in the protecting position.

Because of the angle offset of the needle cannula 12 relative to the longitudinal axis of the reservoir 10, the needle cannula 12 is constantly biased in the direction of the offset such that it will instantly move in that direction when the reservoir 10 is extended sufficiently from the sheath 14 for the tip 36 of the needle cannula 12 to be withdrawn from the needle bore 20. Any attempt to move the reservoir 10 back into the reservoir bore 22 of the sheath 14 would therefore result in the tip 36 of the needle cannula 12 abutting the forward wall 56 of the reservoir bore 22.

The angle offset of the needle cannula 12 relative to the longitudinal axis of the reservoir 10 is formed in the preferred embodiment by forming a bend 58 near the proximal end of the needle cannula 12. Those skilled in the art will recognize that other methods of forming the angle offset, e.g. inserting a straight needle into the distal end 50 of the reservoir 10 at an offset, are likewise suitable.

Travel of the reservoir 10 as it is being withdrawn from the sheath 14 is limited by the rear walls 68 of the channels 52 which abut the detents 32 of the reservoir 10 and thereby prevent the reservoir 10 from being completely withdrawn from the sheath 14.

Referring now to FIG. 5, use of the needle-safe flashback chamber of the present invention with the particular vascular/venous access device disclosed in pending U.S. patent application Ser. No. 07/669,679 is illustrated. The needle cannula 12 of the needle-safe flashback chamber of the present invention is inserted through the wall of an over-the-needle catheter 62 such that the tip 36 extends from the distal end 64 of the catheter 62. Thus, the needle cannula 12 and catheter 62 may be simultaneously inserted into a patient's vein or vascular system. The needle-safe flashback chamber of the present invention provides an indication of flashback when the tip 36 of the needle catheter 12 penetrates the vein. The needle-safe flashback chamber of the present invention may then be withdrawn from the vein and catheter 62, preferably by simultaneously withdrawing the needle cannula 20 from the vein and catheter 62 while also pulling the knob 66 of the reservoir 10 such that needle catheter 12 is withdrawn into the reservoir bore 22 of the sheath 14. Ideally, the needle cannula 12 will be captured within the sheath 14 at approximately the same instant that it is withdrawn from the catheter 62. Thus, the accidental exposure to administering personnel of such substantial health risks as the AIDS virus, hepatitis, and other infectious diseases, is mitigated.

Alternatively, the plug 28 may be removed from the Luer lock 26 such that medication may be administered intravenously to the patient through the flashback chamber of the present invention.

Referring now to FIG. 6, use of the needle-safe flashback chamber of the present invention with a conventional over-the-needle catheter 42 is illustrated. In use the needle cannula 12 would be inserted fully into the catheter 42 such that the tip 36 of the needle cannula 12 extends therethrough. The needle cannula 12 and the catheter 42 would then be inserted into a patient's vein after which the needle cannula 12 could be withdrawn therefrom. The substantially transparent reservoir 10 provides an indication of the tip 36 of the needle 12 entering the vein as blood is observed entering the reservoir 10.

As was done in the practice of the present invention with the catheter disclosed in U.S. patent application Ser. No. 07/669,679, the needle-safe flashback chamber of the present invention may be withdrawn from the conventional catheter 42 while simultaneously pulling the knob 66 of the reservoir 10 to cause the needle cannula 12 to withdraw into the sheath 14 such that the needle cannula 12 preferably becomes locked within the sheath 14 at approximately the same instant as the needle-safe flashback chamber is removed from the conventional catheter 42.

In general, the method of the present invention may be practiced by: inserting a needle cannula and catheter into a vein, the needle cannula having a flashback chamber attached thereto; substantially surrounding the flashback chamber with a sheath; and withdrawing the needle cannula from the catheter while simultaneously covering the needle cannula with the sheath.

Alternatively, a substantially transparent sheath may be placed around the flashback chamber prior to inserting the needle cannula and catheter into a vein. The flashback chamber is preferably slidably disposable within the sheath. The flashback chamber is also preferably disposed within the sheath such that the needle cannula extends through an aperture formed in the sheath and the needle cannula is withdrawn through the aperture formed in the sheath while simultaneously being withdrawn from the catheter such that upon completely withdrawing the needle cannula through the aperture formed in the sheath, the needle cannula becomes misaligned with the aperture formed in the sheath to prevent the needle cannula from extending from the sheath.

The method of the present invention may also be practiced in accordance with the invention disclosed in U.S. patent application Ser. No. 07/669,679, by: inserting a needle cannula through the wall of a catheter such that the distal end of the needle cannula extends from the distal end of the catheter and the proximal end of the needle cannula extends through the wall of the catheter, the needle cannula having a flashback chamber attached thereto; selectively collapsing the catheter about the needle cannula to prevent relative axial movement between the catheter and the needle cannula, such that the needle cannula and catheter may be inserted into a vein; substantially surrounding the flashback chamber with a sheath; and withdrawing the needle cannula from the catheter while simultaneously covering the needle cannula with the sheath. As discussed in the general practice of the present invention above, a substantially transparent sheath may alternatively be placed around the flashback chamber prior to inserting the needle cannula into the catheter. The flashback chamber is preferably slidably disposed within the sheath. The flashback chamber is also preferably disposed within the sheath such that the needle cannula extends through an aperture formed in the sheath and the needle cannula is withdrawn through the aperture formed in the sheath while simultaneously being withdrawn from the catheter such that upon completely withdrawing the cannula through the aperture in the sheath, the needle cannula becomes misaligned with the aperture formed in the sheath to prevent the needle cannula from extending from the sheath.

It is understood that the exemplary needle-safe flashback chamber of the present invention described herein and shown in the drawings represents only a presently preferred embodiment of the invention. Indeed, various modifications and additions may be made to such embodiment without departing from the spirit and scope of the invention. For example, the device need not be configured as a cylinder, i.e. having a circular cross-section, rather those skilled in the art will recognize that other cross-sections, e.g. square and triangular, are likewise suitable. Also, the needle cannula need not be bent at a single spot as illustrated, but rather may bend gradually over a portion of its length. Thus, these and other modifications and additions may be obvious to those skilled in the art and may be implemented to adapt the present invention for use in a variety of different applications.

What is claimed is:

1. A needle-safe flashback chamber for use with a vascular/venous access device comprising:
    a) a reservoir;

b) a needle cannula in fluid communication with said reservoir;

c) a sheath into which said reservoir is slidably disposable;

d) wherein said sheath has a non-protecting position relative to said needle cannula in which said needle cannula extends outward from said sheath;

e) wherein said sheath has a protecting position relative to said needle cannula in which said needle cannula is captured within said sheath;

f) an aperture formed in said sheath such that said needle cannula extends through said aperture when said sheath is disposed in the non-protecting position; and g) wherein said needle cannula is attached to said reservoir at an angle offset from the longitudinal axis of said reservoir such that disposing said sheath in the protecting position causes said needle cannula to exit said aperture and to move to a position such that an attempt to dispose said sheath in the non-protecting position results in misalignment of said needle cannula and said aperture to lock said sheath in the protecting position.

2. The needle-safe flashback chamber as recited in claim 1 further comprising a bend formed in said needle cannula such that said needle cannula is substantially disposed at an angle to the longitudinal axis of said reservoir.

3. The needle-safe flashback chamber as recited in claim 2 further comprising a detent means formed on said reservoir and a complimentary channel means formed within said sheath, said detent and said channel cooperating to prevent rotation of said needle cannula relative to said sheath.

4. The needle-safe flashback chamber as recited in claim 3 wherein said detent means and said channel means cooperate to prevent said reservoir from being withdrawn completely from said sheath.

5. The needle-safe flashback chamber as recited in claim 4 wherein:

a) said detent means comprises at least two detents extending from the distal portion of said reservoir; and b) said channel means comprises at least two complimentary channels formed along a substantial length of said sheath.

6. The needle-safe flashback chamber as recited in claim 5 further comprising:

a) a finger stop formed near the distal end of said sheath to facilitate insertion of said needle;

b) a finger stop formed near the proximal end of said sheath to facilitate positioning of said sheath in the protecting position; and c) a knob formed upon the proximal end of said reservoir to facilitate the withdrawal of said needle.

7. The needle-safe flashback chamber as recited in claim 6 further comprising a vent disposed at the proximal end of said reservoir.

8. The needle-safe flashback chamber as recited in claim 7 further comprising:

a) an aperture formed at the proximal end of said reservoir;

b) a plug configured to be received by said aperture; and c) wherein said vent is formed in said plug.

9. The needle-safe flashback chamber as recited in claim 8 wherein said aperture formed on the proximal end of said reservoir comprises a Luer lock.

10. The needle-safe flashback chamber as recited in claim 9 further comprising a filter disposed within said vent.

11. The needle-safe flashback chamber as recited in claim 10 wherein said filter comprises a hydrophobic material.

12. A method for removing a needle cannula and flashback chamber from a catheter comprising the steps of:

a) substantially surrounding said flashback chamber with a sheath; and b) withdrawing said needle cannula from said catheter while simultaneously covering said needle cannula with said sheath.

13. The method as recited in claim 12 wherein:

a) said sheath is substantially transparent; and b) the step of substantially surrounding said flashback chamber with a sheath is performed prior to inserting said needle catheter into a vein.

14. The method as recited in claim 13 wherein the step of substantially surrounding said flashback chamber with a sheath comprises slidably disposing said flashback chamber within said sheath.

15. The method as recited in claim 14 wherein:

a) the step of disposing said flashback chamber within said sheath comprises disposing said flashback chamber within said sheath such that said needle cannula extends through an aperture formed in said sheath; and b) the step of withdrawing said needle cannula from said catheter while simultaneously covering said needle cannula with said sheath comprises withdrawing said needle cannula through said aperture formed on said sheath;

c) wherein upon completely withdrawing said needle cannula through said aperture formed in said sheath said needle cannula becomes misaligned with said aperture formed in said sheath to prevent said needle cannula from extending from said sheath.

16. A method for inserting a vascular/venous access device comprising:

a) inserting a needle cannula through the wall of a catheter such that the distal end of the needle cannula extends from the distal end of the catheter and the proximal end of the needle cannula extends through the wall of the catheter, said needle cannula having a flashback chamber attached thereto;

b) selectively collapsing said catheter about said needle cannula to prevent relative axial movement between said catheter and said needle cannula, such that said needle cannula and catheter may be inserted into a vein;

c) substantially surrounding said flashback chamber with a sheath; and d) withdrawing said needle cannula from said catheter while simultaneously covering said needle cannula with said sheath.

17. The method as recited in claim 16 wherein:

a) said sheath is substantially transparent; and b) the step of substantially surrounding said flashback chamber with a sheath is performed prior to inserting said needle catheter into a vein.

18. The method as recited in claim 17 wherein the step of substantially surrounding said flashback chamber with a sheath comprises slidably disposing said flashback chamber within said sheath.

19. The method as recited in claim 18 wherein:

a) the step of disposing said flashback chamber within said sheath comprises disposing said flashback chamber within said sheath such that said needle cannula extends through an aperture formed in said sheath; and b) the step of withdrawing said needle cannula from said catheter while simultaneously covering said needle cannula with said sheath comprises withdrawing said needle cannula through said aperture formed in said sheath;

c) wherein upon completely withdrawing said needle cannula through said aperture formed in said sheath said needle cannula becomes misaligned with said aperture to prevent said needle cannula from extending from said sheath.

20. A needle-safe flashback chamber for use with a vascular/venous access device comprising:

a) a reservoir;

b) a needle cannula in fluid communication with said reservoir said needle cannula being attached to said reservoir at an angle offset from the longitudinal axis of the reservoir;

c) a sheath into which said reservoir is slidably disposable, said sheath comprising a forward wall having an aperture through which said needle cannula extends;

d) wherein said sheath has a non-protecting position relative to said needle cannula in which said needle cannula extends outward from said sheath;

e) wherein said sheath has a protecting position relative to said needle cannula wherein said needle cannula and said sheath cooperate to capture said needle cannula within said sheath; and f) wherein said needle cannula moves out of alignment with said aperture when said sheath is disposed in the protecting position, such that said forward wall prevents said needle cannula from extending therefrom after said needle cannula has been disposed in the protecting position.

21. The needle-safe flashback chamber as recited in claim 20 wherein said sheath prevents said needle cannula from extending therefrom after said sheath has been disposed in the protecting position.

22. The needle-safe flashback chamber as recited in claim 20 wherein:

a) said sheath comprises a forward wall having an aperture through which said needle cannula extends; and b) said needle cannula moves out of alignment with said aperture when said sheath is disposed in the protecting position, such that said forward wall prevents said needle cannula from extending therefrom after said needle cannula has been disposed in the protecting position.

* * * * *